United States Patent
Hosszú et al.

(10) Patent No.: US 10,864,024 B2
(45) Date of Patent: Dec. 15, 2020

(54) SPINAL REPOSITIONING INSTRUMENT, SPINAL REPOSITIONING SYSTEM, AND METHODS OF USING THESE

(71) Applicant: Aesculap AG, Tuttlingen (DE)

(72) Inventors: Tomáš Hosszú, Hradec Králové (CZ); Aleš Bezrouk, Hradec Králové (CZ)

(73) Assignee: AESCULAP AG, Tuttlingen (DE)

( * ) Notice: Subject to any disclaimer, the term of this patent is extended or adjusted under 35 U.S.C. 154(b) by 36 days.

(21) Appl. No.: 16/256,745

(22) Filed: Jan. 24, 2019

(65) Prior Publication Data
US 2019/0231399 A1 Aug. 1, 2019

(30) Foreign Application Priority Data

Jan. 26, 2018 (EP) ..................... 18153641

(51) Int. Cl.
*A61B 17/70* (2006.01)
*A61B 17/02* (2006.01)
*A61B 90/00* (2016.01)

(52) U.S. Cl.
CPC ........ *A61B 17/7076* (2013.01); *A61B 17/025* (2013.01); *A61B 17/708* (2013.01); *A61B 17/7077* (2013.01); *A61B 17/7083* (2013.01); *A61B 2017/0256* (2013.01); *A61B 2090/067* (2016.02)

(58) Field of Classification Search
CPC ............. A61B 17/70; A61B 17/7074–17/7082
See application file for complete search history.

(56) References Cited

U.S. PATENT DOCUMENTS

| 7,275,336 | B2 * | 10/2007 | Casutt | A61B 90/06 33/512 |
| 7,811,288 | B2 * | 10/2010 | Jones | A61B 17/7002 606/86 A |
| 7,981,115 | B2 * | 7/2011 | Justis | A61B 90/06 606/102 |

(Continued)

FOREIGN PATENT DOCUMENTS

| WO | 9002527 A1 | 3/1990 |
| WO | 2017093497 A1 | 6/2017 |
| WO | 2017194470 A1 | 11/2017 |

OTHER PUBLICATIONS

Extended European Search Report for European Application No. 18 153 641.8, dated Jul. 5, 2018—9 pages.

*Primary Examiner* — Eduardo C Robert
*Assistant Examiner* — Michelle C Eckman (57) ABSTRACT

A spinal repositioning instrument includes a first coupling body for direct or indirect coupling to a pedicle screw, and a second coupling body for direct or indirect coupling to another pedicle screw. The spinal repositioning instrument can perform a first movement and a second movement independent from the first movement Under the first movement, the coupling bodies perform a scissor-like pivoting about a first axis. Under the second movement, the coupling bodies rotate in opposite directions about respective second axes. The second axes are relatively fixed under the second movement. The spinal repositioning instrument can also include a synchronising transmission such that the rotations of the coupling bodies under the second movement are symmetrical to each other.

18 Claims, 4 Drawing Sheets

(56) References Cited

U.S. PATENT DOCUMENTS

| | | | | |
|---|---|---|---|---|
| 8,157,809 B2* | 4/2012 | Butters | A61B 17/7001 | 606/105 |
| 8,221,426 B2* | 7/2012 | Justis | A61B 17/708 | 606/86 A |
| 8,226,554 B2* | 7/2012 | McBride | A61B 1/32 | 600/219 |
| 8,394,109 B2* | 3/2013 | Hutton | A61B 17/708 | 606/105 |
| 8,460,301 B2* | 6/2013 | Fiorella | A61B 17/7089 | 606/86 A |
| 8,512,343 B2* | 8/2013 | Dziedzic | A61B 17/7089 | 606/86 A |
| 8,608,782 B1* | 12/2013 | Rovner | A61B 17/708 | 606/264 |
| 8,672,944 B2* | 3/2014 | Boachie-Adjei | A61B 17/708 | 606/246 |
| 8,900,247 B2* | 12/2014 | Tseng | A61B 17/15 | 606/102 |
| 8,936,615 B2* | 1/2015 | Pappalardo | A61B 17/8019 | 606/207 |
| 9,060,825 B2* | 6/2015 | Hutton | A61B 17/7032 | |
| 9,216,016 B2* | 12/2015 | Fiechter | A61B 17/7077 | |
| 9,381,051 B2* | 7/2016 | Walker | A61B 17/7086 | |
| 9,408,641 B2* | 8/2016 | Zhang | A61B 17/7023 | |
| 9,480,504 B1* | 11/2016 | Schafer | A61B 17/7083 | |
| 9,622,795 B2* | 4/2017 | Reitblat | A61B 17/0206 | |
| 9,744,050 B1* | 8/2017 | Reitblat | A61F 2/4455 | |
| 9,795,370 B2* | 10/2017 | O'Connell | A61B 17/02 | |
| 9,861,393 B2* | 1/2018 | Ibrahim | A61B 17/8605 | |
| 9,974,577 B1* | 5/2018 | Smith | A61B 17/7076 | |
| 10,194,960 B1* | 2/2019 | Hammann | A61B 17/7086 | |
| 10,390,862 B2* | 8/2019 | Bobbitt | A61B 17/708 | |
| 10,420,593 B2* | 9/2019 | Wall | A61B 17/7079 | |
| 10,499,897 B2* | 12/2019 | Truckey | A61B 17/025 | |
| 10,517,644 B2* | 12/2019 | Fessler | A61B 17/888 | |
| 2005/0021040 A1 | 1/2005 | Bertagnoli | A61B 17/025 | 606/90 |
| 2005/0203533 A1* | 9/2005 | Ferguson | A61B 17/025 | 606/90 |
| 2005/0245928 A1* | 11/2005 | Colleran | A61B 17/708 | 606/90 |
| 2006/0036255 A1* | 2/2006 | Pond, Jr. | A61B 17/7079 | 606/86 R |
| 2006/0149236 A1* | 7/2006 | Barry | A61B 17/7077 | 606/86 A |
| 2006/0195092 A1* | 8/2006 | Barry | A61B 17/7077 | 606/86 A |
| 2006/0200132 A1* | 9/2006 | Chao | A61B 17/708 | 606/86 A |
| 2006/0247645 A1* | 11/2006 | Wilcox | A61B 17/025 | 606/86 R |
| 2006/0247649 A1* | 11/2006 | Rezach | A61B 17/7077 | 606/90 |
| 2007/0093828 A1* | 4/2007 | Abdou | A61B 17/025 | 606/86 A |
| 2007/0093846 A1* | 4/2007 | Frigg | A61B 17/025 | 606/90 |
| 2007/0173831 A1* | 7/2007 | Abdou | A61B 17/3211 | 606/279 |
| 2007/0191856 A1* | 8/2007 | Gil | A61B 17/025 | 606/90 |
| 2007/0213715 A1* | 9/2007 | Bridwell | A61B 17/025 | 606/264 |
| 2007/0213716 A1* | 9/2007 | Lenke | A61B 17/025 | 606/264 |
| 2008/0077138 A1* | 3/2008 | Cohen | A61B 17/708 | 606/86 A |
| 2008/0077155 A1* | 3/2008 | Diederich | A61B 17/708 | 606/105 |
| 2008/0119852 A1* | 5/2008 | Dalton | A61B 17/7032 | 606/86 R |
| 2008/0119862 A1* | 5/2008 | Wicker | A61B 17/708 | 606/99 |
| 2008/0177270 A1* | 7/2008 | Sorrenti | A61B 17/025 | 606/90 |
| 2008/0255567 A1* | 10/2008 | Accordino | A61B 17/86 | 606/90 |
| 2008/0262494 A1* | 10/2008 | Moore | A61B 17/7077 | 606/53 |
| 2008/0294206 A1* | 11/2008 | Choi | A61B 17/708 | 606/86 A |
| 2009/0062857 A1* | 3/2009 | Ramsay | A61B 17/1735 | 606/246 |
| 2009/0149892 A1* | 6/2009 | Stad | A61B 17/708 | 606/86 A |
| 2009/0228053 A1* | 9/2009 | Kolb | A61B 17/7076 | 606/86 A |
| 2010/0004695 A1* | 1/2010 | Stad | A61B 17/708 | 606/86 A |
| 2010/0030283 A1* | 2/2010 | King | A61B 17/7037 | 606/86 A |
| 2010/0042149 A1* | 2/2010 | Chao | A61B 17/7079 | 606/246 |
| 2010/0262198 A1* | 10/2010 | Braunschweiler | A61B 17/7005 | 606/86 A |
| 2010/0274252 A1* | 10/2010 | Bottomley | A61B 17/708 | 606/90 |
| 2010/0312279 A1* | 12/2010 | Gephart | A61B 17/3421 | 606/264 |
| 2010/0331849 A1* | 12/2010 | Riesinger | A61B 17/7077 | 606/90 |
| 2011/0077689 A1* | 3/2011 | Mickiewicz | A61B 17/7047 | 606/277 |
| 2011/0106082 A1* | 5/2011 | Kave | A61B 17/708 | 606/70 |
| 2011/0130793 A1* | 6/2011 | Woolley | A61B 17/0206 | 606/279 |
| 2011/0224734 A1* | 9/2011 | Schelling | A61B 17/7079 | 606/286 |
| 2012/0035668 A1* | 2/2012 | Manninen | A61B 17/7037 | 606/305 |
| 2012/0071885 A1* | 3/2012 | Forton | A61B 17/708 | 606/104 |
| 2012/0191143 A1* | 7/2012 | Nayet | A61B 17/708 | 606/86 A |
| 2012/0197297 A1* | 8/2012 | Bootwala | A61B 17/7077 | 606/246 |
| 2012/0203279 A1* | 8/2012 | Walters | A61B 17/7077 | 606/252 |
| 2012/0221057 A1* | 8/2012 | Zhang | A61B 17/701 | 606/264 |
| 2012/0239096 A1* | 9/2012 | Gleeson | A61B 17/708 | 606/86 A |
| 2012/0253402 A1* | 10/2012 | McLean | A61B 17/7032 | 606/264 |
| 2012/0265212 A1* | 10/2012 | Seck | A61B 17/708 | 606/102 |
| 2012/0271308 A1* | 10/2012 | Dominik | A61B 17/7077 | 606/59 |
| 2012/0296171 A1* | 11/2012 | Lovell | A61B 17/0206 | 600/213 |
| 2013/0090691 A1* | 4/2013 | Zhang | A61B 17/7079 | 606/264 |
| 2013/0096635 A1* | 4/2013 | Wall | A61B 17/7079 | 606/305 |
| 2013/0110184 A1* | 5/2013 | Wing | A61B 17/708 | 606/86 A |
| 2013/0172947 A1* | 7/2013 | Greenberg | A61B 17/708 | 606/86 A |
| 2013/0184763 A1* | 7/2013 | McClintock | A61B 17/88 | 606/279 |
| 2013/0211453 A1* | 8/2013 | Lenke | A61B 17/708 | 606/250 |
| 2013/0245692 A1* | 9/2013 | Hayes | A61B 17/025 | 606/279 |

(56) References Cited

U.S. PATENT DOCUMENTS

| | | | |
|---|---|---|---|
| 2013/0289633 A1* | 10/2013 | Gleeson | A61B 17/7074 606/86 A |
| 2014/0039556 A1* | 2/2014 | Rutschmann | A61B 17/7002 606/266 |
| 2014/0039567 A1* | 2/2014 | Hoefer | A61B 17/7083 606/86 A |
| 2014/0046372 A1* | 2/2014 | Ibrahim | A61B 17/7034 606/250 |
| 2014/0074106 A1* | 3/2014 | Shin | A61B 17/7079 606/104 |
| 2014/0100611 A1* | 4/2014 | Barry | A61B 17/7032 606/265 |
| 2014/0100613 A1* | 4/2014 | Iott | A61B 17/7086 606/279 |
| 2014/0100619 A1* | 4/2014 | DiPaola | A61B 17/7076 606/86 R |
| 2014/0107656 A1* | 4/2014 | Masson | A61B 17/56 606/90 |
| 2014/0107659 A1* | 4/2014 | Walters | A61B 17/7074 606/102 |
| 2014/0107707 A1* | 4/2014 | Rovner | A61B 17/7034 606/264 |
| 2014/0114354 A1* | 4/2014 | May | A61B 17/7077 606/246 |
| 2014/0249591 A1* | 9/2014 | Peultier | A61B 17/7077 606/86 A |
| 2014/0257312 A1* | 9/2014 | Solitario, Jr. | A61B 17/7079 606/90 |
| 2014/0277151 A1* | 9/2014 | Fowler | A61B 17/7074 606/265 |
| 2014/0277198 A1* | 9/2014 | Stad | A61B 17/7074 606/86 A |
| 2014/0316475 A1* | 10/2014 | Parikh | A61B 17/7085 606/86 A |
| 2014/0343561 A1* | 11/2014 | Penzimer | A61B 17/7074 606/102 |
| 2014/0350612 A1* | 11/2014 | Leroux | A61B 17/708 606/86 A |
| 2015/0057712 A1* | 2/2015 | Hsueh | A61B 17/7074 606/86 A |
| 2015/0066042 A1* | 3/2015 | Cummins | A61B 17/7037 606/104 |
| 2015/0066088 A1* | 3/2015 | Brinkman | A61B 17/7077 606/264 |
| 2015/0112399 A1* | 4/2015 | Peukert | A61B 17/708 606/86 A |
| 2015/0201974 A1* | 7/2015 | Deridder | A61B 17/7074 606/102 |
| 2015/0320458 A1* | 11/2015 | Rezach | A61B 17/7077 606/279 |
| 2016/0000478 A1* | 1/2016 | Fischer | A61B 17/708 606/279 |
| 2016/0089188 A1* | 3/2016 | McBride, Jr. | A61B 17/7085 606/279 |
| 2016/0095634 A1* | 4/2016 | Meyer | A61B 17/7077 606/86 A |
| 2016/0242827 A1* | 8/2016 | Viljoen | A61B 17/7052 |
| 2016/0262807 A1* | 9/2016 | Benson | A61B 17/7077 |
| 2016/0262810 A1* | 9/2016 | Meyer | A61B 17/7076 |
| 2016/0278821 A1* | 9/2016 | Artaki | A61B 17/708 |
| 2016/0345952 A1* | 12/2016 | Kucharzyk | A61B 17/708 |
| 2016/0354073 A1* | 12/2016 | Nel | A61B 17/02 |
| 2017/0000530 A1* | 1/2017 | McNally | A61B 17/7077 |
| 2017/0020583 A1* | 1/2017 | Tsai | A61B 17/7032 |
| 2017/0042524 A1* | 2/2017 | Angus | A61B 17/025 |
| 2017/0112539 A1* | 4/2017 | Hayes | A61B 17/708 |
| 2017/0224392 A1* | 8/2017 | Choi | A61B 17/7079 |
| 2017/0296160 A1* | 10/2017 | O'Brien | A61B 17/025 |
| 2017/0311985 A1* | 11/2017 | Bobbitt | A61B 17/708 |
| 2017/0311995 A1* | 11/2017 | Wall | A61B 17/708 |
| 2018/0021070 A1* | 1/2018 | Wall | A61B 17/7002 606/86 A |
| 2018/0049774 A1* | 2/2018 | Farmer | A61B 17/708 |
| 2018/0070993 A1* | 3/2018 | Leff | A61B 17/7079 |
| 2018/0070994 A1* | 3/2018 | Leff | A61B 17/7049 |
| 2018/0110504 A1* | 4/2018 | McAfee | A61B 17/7077 |
| 2018/0168565 A1* | 6/2018 | Miller | A61B 17/7077 |
| 2018/0185067 A1* | 7/2018 | Ohnmacht | A61B 17/708 |
| 2018/0185072 A1* | 7/2018 | Rubin | A61B 17/708 |
| 2018/0206891 A1* | 7/2018 | Hsueh | A61B 17/7083 |
| 2018/0214189 A1* | 8/2018 | Olea | A61B 17/7001 |
| 2018/0228520 A1* | 8/2018 | Bobbitt | A61B 17/7002 |
| 2018/0256214 A1* | 9/2018 | Dejardin | A61B 17/7055 |
| 2018/0271566 A1 | 9/2018 | Fischer et al. | |
| 2019/0110785 A1* | 4/2019 | Serokosz | A61B 17/0206 |
| 2019/0231394 A1* | 8/2019 | Bechtel | A61B 17/025 |
| 2019/0231399 A1* | 8/2019 | Hossz | A61B 17/025 |
| 2019/0290330 A1* | 9/2019 | Combrowski | A61F 2/4611 |
| 2019/0336182 A1* | 11/2019 | Suh | A61B 17/7002 |
| 2019/0380748 A1* | 12/2019 | Doose | A61B 17/7082 |

* cited by examiner

SPINAL REPOSITIONING INSTRUMENT, SPINAL REPOSITIONING SYSTEM, AND METHODS OF USING THESE

RELATED APPLICATION

This application claims the benefit of priority of European Application No. 18 153 641.8, the contents of which is incorporated by reference herein in its entirety.

FIELD

The present disclosure relates to a repositioning instrument and a repositioning system, for spinal column surgery, in particular for the minimally-invasive correction of spinal column fractures with the help of a dorsal stabilization system. The present disclosure also relates to a method of using the repositioning instrument, and a method of using the repositioning system.

BACKGROUND

Spinal disorders such as vertebral fractures and degenerative diseases require surgery to stabilize the spine to promote healing and/or reduce pain. This typically involves anchoring implants such as pedicle screws into the patient's vertebrae; rigid rods are received by the screws' heads; the rods are fixed in place by tightening locking elements such as set screws. In this way at least two vertebral bodies are stabilized. Such a fixing system is known as a dorsal stabilization system.

A main goal of spine stabilization (osteosynthesis) is to achieve the optimal shape/position of the spine for healing. This comprises restoring the spine's physiological curvature, and reshaping any fractured vertebral body to a physiological shape as much as possible. Adjusting the sagittal curve of the back may be done after the pedicle screws have been anchored and before the rods have been fixed. At this stage a repositioning instrument can be attached to the pedicle screws to reposition vertebral bodies.

Vertebral repositioning can comprise distraction—wherein vertebral bodies are linearly separated so as to treat a compression; and reduction—wherein the angle between vertebral bodies is adjusted so as to reduce a kyphotic or lordotic deformity (i.e. for when a fractured vertebral body is kyphotically or lordotically out of position). Reduction is also known as angulation. In the case of fracture repositioning, a combination of distraction and reduction is often required.

In order to be able to carry out a controlled repositioning of the sagittal profile, the distraction and the reduction of the vertebral body should take place independently of each other. Furthermore the repositioning performed by the instrument should be temporarily held until the definitive fixing of the rods in the dorsal stabilization system is complete. Accordingly it is necessary for the new position (reposition) to be maintained right until the dorsal stabilization system has been fixed. Loss of reposition (in the period between these steps, for example) is undesirable.

A pedicle screw usually has an axial, shaft-like external thread section, to which a so-called tulip connects on the screw's screw head side. Repositioning of the vertebral body typically comprises application of a force (for distraction) and application of a moment (for reduction) to one or more tulips. Furthermore the tulip forms a U-shaped longitudinally slotted receiving sleeve with internal thread for receiving the aforementioned rod and locking element.

Basically, two basic types of pedicle screws are distinguished, namely monoaxial and polyaxial pedicle screws. Polyaxial and monoaxial screws share the common feature that forces can be applied to their tulips, enabling distraction. Polyaxial pedicle screws have advantages over monoaxial pedicle screws with respect to handling and adaptability possibilities for inserting the rod, but bring the disadvantage that moments cannot can be applied through the movable tulip which has not yet been fixed/locked. Therefore polyaxial screws tend to be used only in cases of small spinal deformities, and/or when the surgeon intentionally leaves some residual kyphosis; some patients might need further surgery as a result.

A downtube is a longitudinal extension element, for facilitating the fixing of the pedicle screw and rod to a vertebral body. In particular it may comprise a distal end which is designed to temporarily couple with the tulip of a pedicle screw in a known manner; and an outer sleeve which has a slot extending parallel to a longitudinal axis of the outer sleeve. The slot can be aligned with the head in such a way that a rod can be introduced into the tulip.

WO2017093497 A1 discloses a medical instrument having two coupling means which are relatively pivotable. Pivoting is performed by sliding one coupling means along an arc-shaped path while the other coupling means remains fixed. During a spine stabilization procedure two pedicle screws are fixed to respective vertebral bodies. When the medical instrument performs reduction by means of coupling to the pedicle screws, the two vertebral bodies relatively rotate.

Using the arrangement in WO2017093497 A1 brings the disadvantage that although the pivoted vertebral bodies are individually reoriented, their relative positions can remain unchanged. Desirably, a reduction would take place about an intermediate damaged vertebral body acting as a hinge. However in a reduction in practice each vertebra adjacent to the damaged vertebral body rotates about its own respective rotation point; if its position does not also adapt to the new orientation, a vertebral body can be pushed in the anterior-posterior direction, leading to a misalignment corresponding to a Spondylolisthesis. This amounts to an asymmetrical kyphosis reduction wherein shear forces are applied to a vertebral body. This undesired phenomenon is referred to in the following as "anterior-posterior shift". Further measures must then be taken to ensure against a dislocation of the treated segment.

For example when using the above-described medical instrument, any anterior-posterior shift is avoided by limiting the kyphotic reduction (for example to a maximum anterior wedge angle of 20 degrees). Furthermore it is known in the art to be able to treat moderate anterior wedge angles (less than 35 degrees) conservatively (e.g. without surgery), such as in the case of stable compression fractures. Therefore there is a need for a surgical solution for kyphosis angles (anterior wedge angles) over 35 degrees.

A spinal repositioning instrument is known from US20150066088 A1, comprising a first coupling body for direct or indirect coupling to a pedicle screw, and a second coupling body for direct or indirect coupling to another pedicle screw, wherein the spinal repositioning instrument is configured to perform a first movement and a second movement independent from the first movement; under the second movement the coupling bodies rotate in opposite directions about respective second axes; wherein the second axes are relatively fixed under the second movement.

SUMMARY

It is an object of the present disclosure to provide a spinal repositioning instrument, and a spinal repositioning system, which can perform reduction with less anterior-posterior shift being applied to the vertebral bodies; and respective methods of using these. It is a further object to provide a simple construction.

Basically, a spinal repositioning instrument is provided, comprising two coupling bodies being functionally connected to each other to carry out a vertebral repositioning maneuver (first movement) and a reduction/angulation maneuver (second movement) as defined above. The core of the present disclosure lies in configuring the spinal repositioning instrument (instrument) so that under the reduction maneuver (second movement) there is reflectional symmetry in the individual movements/rotations of the two coupling bodies preferably by providing a synchronisation mechanism/transmission (linking/synchronizing the individual movements of the two coupling bodies according to the second movement with each other). Accordingly, the spinal reposition comprises a first coupling body for direct or indirect coupling to a pedicle screw and a second coupling body for direct or indirect coupling to another pedicle screw wherein the spinal reposition instrument is configured to perform a first movement and a second movement independent from the first movement, under the first movement the coupling bodies perform a scissor-like pivoting about a first axis and under the second movement the coupling bodies rotate in opposite directions about respective second axes wherein the two second axes are relatively fixed to each other under the second movement, further comprising a synchronisation transmission being configured such that the rotations of the coupling bodies under the second movement are reflectionally symmetric to each other.

In other words when the second movement is performed the movements of the coupling bodies are mirror-symmetric to each other about a first plane; the coupling bodies themselves need not have reflective symmetry in their structure. Each of the second axes has a fixed position relative to its corresponding coupling body as the coupling body rotates, the second axes being in different positions. Due to the reflectional symmetry of the second movement, as the vertebral bodies reorient, there are no significant shear stresses on the vertebral bodies, compared to the state of the art. Anterior-posterior shift is reduced or completely removed. Taking further measures to prevent dislocation can be avoided; larger kyphotic reduction angles are possible. Furthermore, both the first and the second movements comprise rotation, allowing for a simpler construction, e.g. their mechanisms can comprise common parts. A scissor-like movement can also be described as the movement of the arms of a pair of tongs or forceps. The amount of distraction can be easily controlled by controlling the degree of scissor-like pivoting. There is no need for additional structures for maintaining the parallelism of the coupling bodies (there is no need for a separate linear guiding mechanism). A distraction can be performed with a simply constructed instrument.

As another aspect of the present disclosure, the instrument comprises a linkage mechanism connecting the coupling bodies to allow the first movement. The scissor-like pivoting is facilitated with a simpler construction.

As another aspect of the present disclosures, each coupling body comprises at least one column-like leg portion having a distal end portion to which a pedicle screw can be connected and at least one arc portion or an arc-like leg portion provided at a proximal end portion of the column-like leg portion extending substantially perpendicular to the column-like leg portion and having an arc centre at the second axis of its respective coupling body to be convex into the proximal direction of the column-like leg portion, wherein two arc portions are connected at the linkage mechanism. Therefore it is easier to perform symmetric rotation under the second movement. Since the arc portions are provided on the coupling bodies, rather than on the linkage mechanism, a more compact linkage mechanism is achieved.

As another aspect of the present disclosures, the linkage mechanism is configured to (independently) allow the second movement. So the first and second movements are guided by a single linkage mechanism. A more compact construction is achieved.

As another aspect of the present disclosures, the linkage mechanism is provided at the first axis. Therefore, the construction is even simpler since the linkage mechanism is not provided at a distance from the first axis. Preferably the second axes may be distant from the linkage mechanism, facilitating minimally invasive surgery.

As another aspect of the present disclosures, the linkage mechanism comprises a respective guide for slidingly guiding each arc portion. Therefore the guidance of each arc portion can be individually set and the arc portions are more reliably guided. It is not necessary to provide physical pivot structures for each coupling body at their respective second axes, since an equivalent motion is achieved by the arc portions sliding in the guides.

As another aspect of the present disclosures, the guides are pivotably connected, the pivot being at the first axis. Therefore independence between the first and second movements is facilitated by providing guides, and in addition by the guides being relatively pivotable.

As another aspect of the present disclosures, under the second movement the synchronising transmission is configured to slide two arc portions at the same rate under guidance from the linkage mechanism. In other words, the synchronising transmission and the linkage mechanism can cooperate to slidingly guide two arc portions at the same rate. Therefore symmetry of rotations of the coupling bodies under the second movement is facilitated.

As another aspect of the present disclosures, the synchronising transmission comprises at least one pinion, wherein the two arc portions each comprise a rack surface, respectively and the rack surfaces engage with the pinion. Therefore symmetry of rotations of the coupling bodies under the second movement is mechanically facilitated.

As another aspect of the present disclosures, the pinion can spin about the first axis, which may preferably be the pivot of the guides. The construction is simpler since there is no need to provide the pinion separately from the first axis. Common parts for allowing the first and second movement can be provided.

As another aspect of the present disclosures, the pinion is accommodated in the guides. Therefore the construction is more compact.

As another aspect of the present disclosures, a spinal repositioning system contains at least two spinal repositioning instruments. In this way, when used with polyaxial pedicle screws configured to temporarily lock the tulip (e.g. configured to temporarily lock the tulip without a rod being inserted), a first instrument can be coupled to (the tulips of) pedicle screws on one side of the spine (i.e. on one side of the sagittal plane), and a second instrument can be coupled to (the tulips of) pedicle screws on the other side of the spine. The pedicle screws coupled to one instrument can be in their unlocked states and the same instrument can be adjustable in its second movement/free to move in its second movement, while its first movement is fixed/blocked. The pedicle screws coupled to the other instrument can be in their locked states and the first and second movements of this instrument can be fixed/blocked. Under these conditions the entire system is fixed, i.e. the positions and orientations of the pedicle screw shafts (and so also the vertebral bodies) remain fixed, even if the pedicle screws for the one instrument are unlocked and the same instrument is adjustable/free to move in its second movement. This freedom of movement facilitates tulip adjustments, permitting rod insertion. In this way, due to the unlocked tulips, the alignment between rod and tulips can be always perpendicular and the locking of the rod will be possible in a non-constrained condition. Preferably the spinal repositioning system contains at least four polyaxial pedicle screws; further preferably the polyaxial pedicle screws are temporarily lockable.

As can be gathered from the above, the spinal repositioning instrument according to the present present disclosure comprises a first coupling body adapted for direct or indirect coupling to a pedicle screw, and a second coupling body adapted for direct or indirect coupling to another pedicle screw, wherein the spinal repositioning instrument is configured to perform a first movement for vertebral repositioning under which first movement the first and second coupling bodies are moved respectively for changing a distance between the pedicle screws when being coupled to the coupling bodies and to perform a second movement for reduction independent from the first movement, under which second movement the coupling bodies are moved respectively for changing the angle between the longitudinal axes of the pedicle screws when being coupled to the coupling bodies, and a synchronising mechanism or transmission is provided functionally linking the two coupling bodies with each other and being configured such that at least or exclusively the respective movements of the coupling bodies under the second movement are reflectionally symmetric to each other.

Just optionally, in the spinal repositioning instrument an adjustable linkage mechanism is provided connecting the two coupling bodies such that under the first movement the coupling bodies perform a scissor-like pivoting about a first axis provided by the linkage mechanism in a first adjustment state of the linkage mechanism exclusively allowing the pivoting movement and under the second movement the coupling bodies perform a rotation in opposite directions about respective second axes in a second adjustment state of the linkage mechanism allowing a translation movement of the coupling bodies relative to each other wherein the two second axes are relatively fixed to each other under the second movement.

As another aspect of the present disclosures, a method for using the spinal repositioning instrument according to the present disclosure comprises: attaching two pedicle screws to two vertebral bodies, with one pedicle screw for each vertebral body; coupling each coupling body to a pedicle screw, optionally via a respective downtube; and performing a reduction by moving the spinal repositioning instrument under the second movement. Preferably the reduction may be preceded by a distraction by moving the spinal repositioning instrument under the first movement.

As another aspect of the present disclosures, a method for using the spinal repositioning system comprises: attaching two polyaxial pedicle screws to each one of two vertebral bodies; coupling a first spinal repositioning instrument to two polyaxial pedicle screws on one side of the spine, optionally via downtubes; coupling a second spinal repositioning instrument to two pedicle screws on the other side of the spine, optionally via downtubes; performing a reduction by moving the spinal repositioning instruments under their second movements with the four polyaxial pedicle screws locked.

Preferably the method may be followed by: unlocking the polyaxial pedicle screws coupled to the first spinal repositioning instrument; fixing the first movement of the first spinal repositioning instrument and allowing its second movement; fixing the first and second movements of the second spinal repositioning instrument; and inserting a rod into the tulips of the unlocked polyaxial pedicle screws. In other words the tulips on only one side of the spine are unlocked while the second movement of the repositioning instrument is also possible/opened. The distance between the tulips is still fixed. On the contra-lateral side the repositioning instrument is fully locked. Due to the open tulips the alignment between rod and tulips can be always perpendicular and the locking of the rod will be possible in a non-constrained condition. Rod insertion and/or rod locking is facilitated, even when the rod is not straight.

BRIEF DESCRIPTION OF THE DRAWING FIGURES

Preferred embodiments of the present disclosure will be described in detail with reference to the following figures, wherein.

DETAILED DESCRIPTION

Detailed embodiments are described in the following with reference to the figures, with similar features having corresponding reference numbers.

Figure 1:
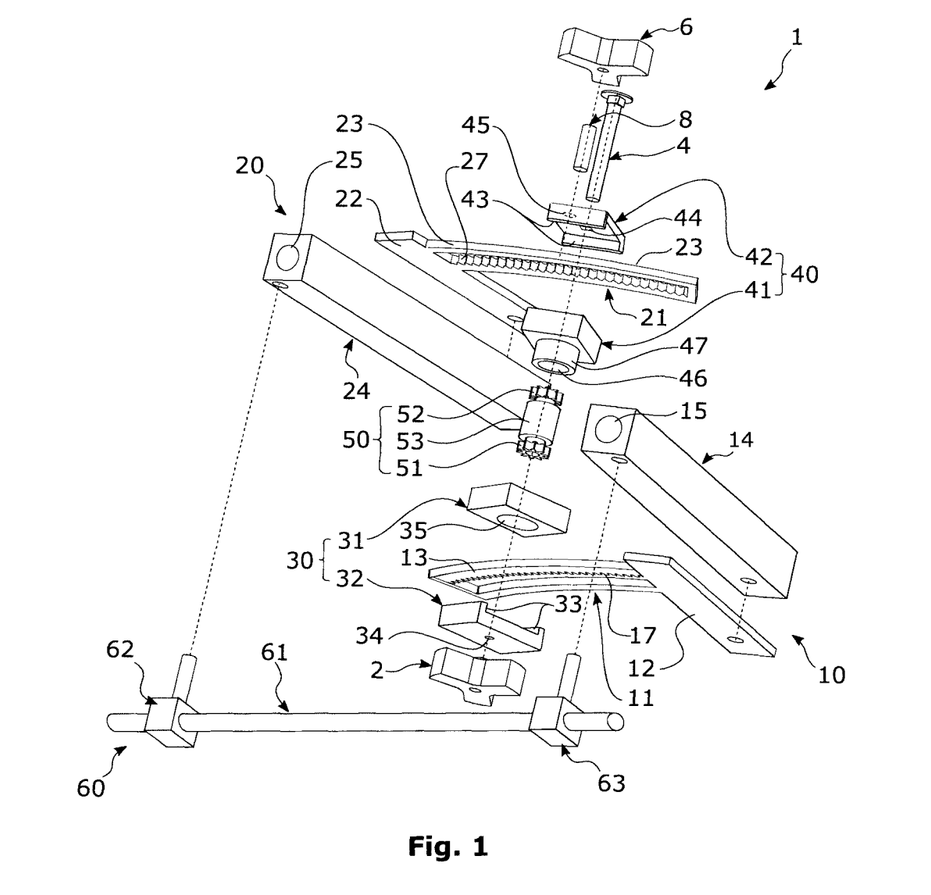
FIG. 1 shows an exploded view of the spinal repositioning instrument according to an embodiment of the present disclosure.
Figure 2:
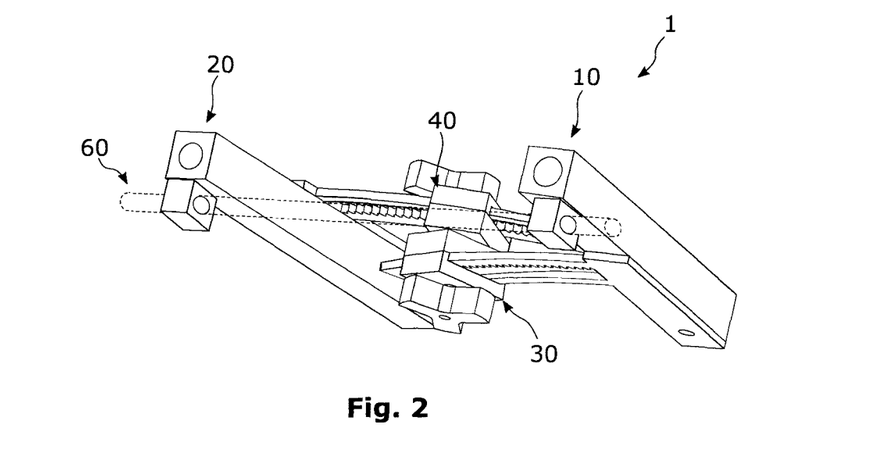
FIG. 2 shows an assembled view of the spinal repositioning instrument.

A spinal repositioning instrument (instrument 1) according to the embodiment is shown exploded in FIG. 1 and fully assembled in FIG. 2. The instrument comprises a first 10 and a second 20 coupling body. Each coupling body 10, 20 comprises a respective column (first column 14 and second column 24). Each column 14, 24 has a respective through hole 15, 25 along its length. One (proximal) end of each column 14, 24 is adapted to be coupled to the tulip of a pedicle screw as known in the prior art, optionally via a downtube (also known in the prior art), and to receive surgical tools (not shown). The instrument 1 may comprise metallic parts.

Each coupling body 10, 20 comprises a plate-like rail (first rail 11 and second rail 21). Each rail has a longitudinal mount portion 12, 22 and an arc portion 13, 23. The mount portion 12, 22 is fixed (e.g. screwed) to a respective column 14, 24 at the proximal end portion thereof. Alternatively a rail 11, 21 may be integrally formed with its column 14, 24 at its proximal end portion. The mount portion 12, 22 may be partly or wholly omitted. Each arc portion 13, 23 extends from a thickness-face of the mount portion 12, 22, part-way along the mount portion, and in a circular arc such that it is substantially perpendicular with respect to the column 14, 24. The extension angle of each arc portion may be, for example, 30 to 45 degrees.

Each arc portion 13, 23 comprises an arc-shaped longitudinally extending recess passing through the entire thickness of the arc portion 13, 23, so as to form four surfaces. The first surface is a radially outwardly facing arcuate surface; the second surface is a radially inwardly facing arcuate surface concentric with the first surface, and the two remaining surfaces are essentially radially straight surfaces that join the ends of the first and second surfaces. The radially outwardly facing arcuate surface of the recess of the arc portion 23, and/or the radially inwardly facing arcuate surface of the recess of the second arc portion 13 are (each) provided with a row of rack teeth 17, 27, preferably having an involute profile.

Figure 3:
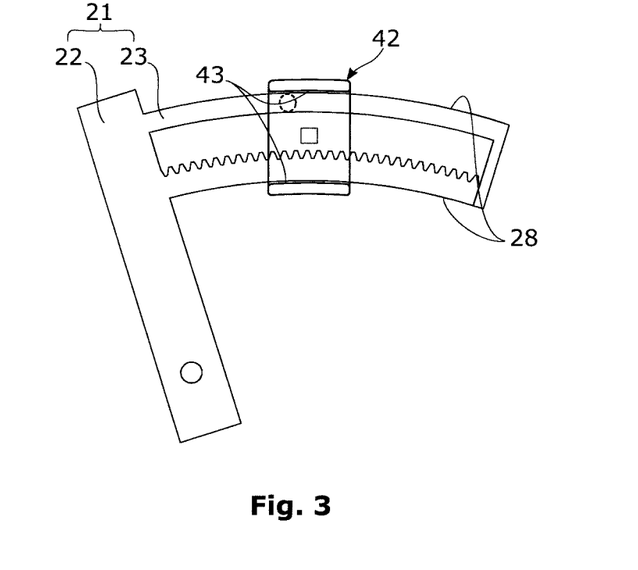
FIG. 3 shows a partial view of the spinal repositioning instrument.

The instrument 1 comprises a first 30 and a second 40 guide which each slidably receive a respective arc portion 13, 23. Each guide 30, 40 comprises a plate (first 32 and second 42 plate) and a block (first 31 and second 41 block) which are fixed together in a known manner (for example by screws which are not shown in the figures). Each plate 32, 42 is provided with a respective pair of arc-shaped bearing surfaces 33, 43, each one having a depth in the plate-thickness direction corresponding to the plate thickness of the arc portion 13, 23, preferably including an additional small clearance to promote ease of sliding. The bearing surfaces 33, 43 each slidably engage with respective peripheral surfaces 28 (shown in FIG. 3) of an arc portion 13, 23. Each bearing surface 33, 43 corresponds to the curve of the peripheral arc portion surface 28 which it faces, optionally with a clearance in the radial direction to promote ease of sliding. The arrangement is shown in FIG. 3, where the second rail's arrangement is shown exemplarily. Alternatively the bearing surfaces 33, 43 may be provided on the blocks 31, 41, or are separate parts from the blocks 31, 41 and plates 32, 42.

Figure 4:
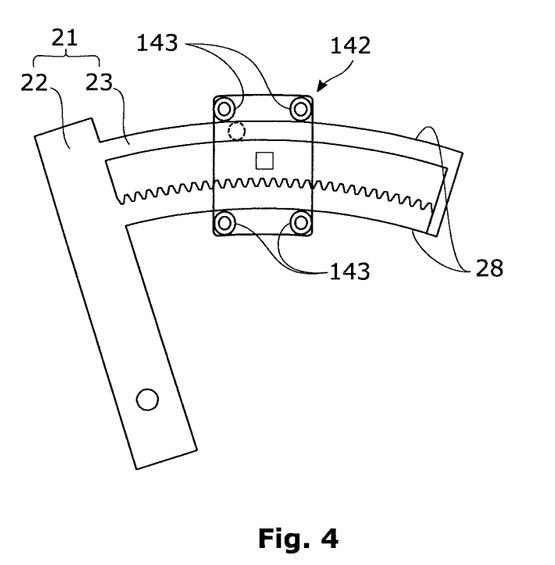
FIG. 4 shows a partial view of a modification to the spinal repositioning instrument.

With reference to FIG. 4, as an optional variant with the advantage of further reducing friction, an arc-shaped bearing surface 43 may be replaced by two or more rotational bearings 143 attached to the plate 142 on the bearings' inner peripheries (such as via a pin provided on the plate 142), and the bearings' rotatable outer peripheries engage with the peripheral surface of an arc portion 23. The rotational bearings 143 may be plain bearings or rolling element bearings, for example.

Returning to FIG. 1, planar surfaces of each guide 30, 40 function as further bearing surfaces which engage with planar surfaces of the arc portions 13, 23 so as to constrain each arc portion 13, 23 to move in a respective plane.

The block of the first guide (first block 31) is provided with a through-hole 35 and the block of the second guide 40 (second block 41) is provided with a cylindrical boss 47 insertable in the through-hole 35 so that pivoting is allowed between the guides 30, 40. Optionally a low friction sleeve may be provided between the peripheral contact surfaces of the through-hole 35 and the boss 47. Alternatively a rolling element bearing may be provided instead of a low-friction sleeve. The second block 41 comprises a through-hole 46 concentric with the boss 47.

The instrument 1 comprises an essentially cylindrical pinion 50 having a through-hole, a periphery 53 and two toothed (preferably involute-toothed) peripheral portions 51, 52 provided at axial end portions. The pinion 50 is rotatably inserted in the through-holes 35, 46 of the blocks so that the pinion's toothed portions 51, 52 protrude from these to each lie in a respective recess of the arc portions 13, 23. In this way each toothed portion 51, 52 engages with the rack teeth 17, 27 of a respective arc portion 13, 23. Axial movement of the pinion 50 is restricted by the planar surfaces of the plates 32, 42, which face each other. The rack teeth and pinion form part of a synchronising transmission.

The first plate 32 is provided with a threaded through-hole 34 extending in the plate-thickness direction. The second plate 42 is provided with a threaded through-hole 45 and an unthreaded through-hole 44, both extending in the plate-thickness direction.

A bolt 4 is inserted in all of: the through-holes 34, 44 in the plates 32, 42; the through-holes 35, 46 in the blocks 31, 41; the recesses of the arc portions 13, 23, and the through-hole in the pinion 50. The though-hole 44 of the second plate 42 is configured to restrict the bolt's rotation. For example the though-hole 44 may be square and a portion of the bolt 4 may have a square section. Alternatively or in addition the bolt 4 may be welded to the second plate 32.

A first 2 and a second 6 nut, preferably wing nuts, are provided at the first 32 and second plates 42 respectively, each nut 2, 6 having a threaded hole. The first nut 2 engages with the bolt 4 and is tightenable by a tool or by hand. Tightening the first nut 2 brings together the mutually facing surfaces of the first 31 and second 41 blocks so that their rotation is blocked due to friction. Preferably these surfaces may be treated with a high-friction coating or suitable surface finish, for example. Any suitable means known in the art may be used to allow the relative rotation of the guides 30, 40 to be temporarily blocked. The guides form part of a linkage mechanism.

The second nut 6 is screwed into the threaded hole 45 of the second plate 32 via a threaded pin 8. Rotation between the threaded pin 8 and the second nut 6 is blocked by means known in the art, e.g. welding or bonding. Alternatively the threaded pin 8 is integrally formed with the second nut 6. By tightening the second nut 6, e.g. by a tool or by hand, the end of the threaded pin 8 farther from the second nut 6 impinges on a planar surface of the second arc portion 23 so as to block the same from sliding through the second guide 40, by friction. Thus sliding of the first arc portion 13 through the first guide 40 is also blocked, since the sliding of the arc portions 13, 23 is synchronised through rotation of the pinion 50. Preferably the end face of the threaded pin 8 impinging on the second arc portion 23 may be made from a softer material than the second arc portion, such as brass or polymer, so as to reduce surface damage to the second arc portion. Further preferably the impinging surface area and materials may be chosen in view of optimising friction. Optionally the sliding motion of the arc portions 13, 23 may be blocked by directly blocking the rotation of the pinion 50. Any suitable means known in the art may be used to allow the sliding motion of the arc portions 13, 23 to be temporarily blocked.

Figure 5:
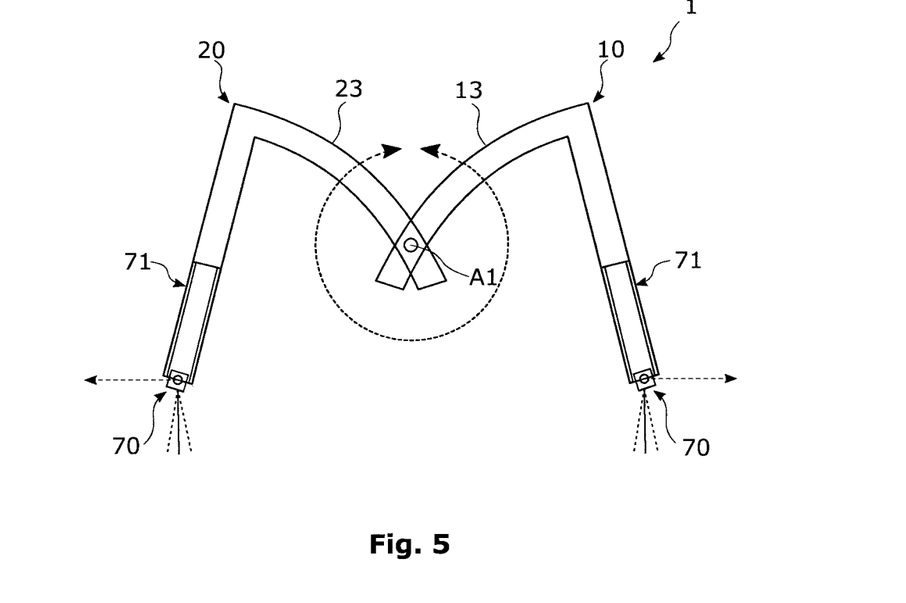
FIG. 5 shows a schematic view of a first movement of the spinal repositioning instrument.
Figure 6:
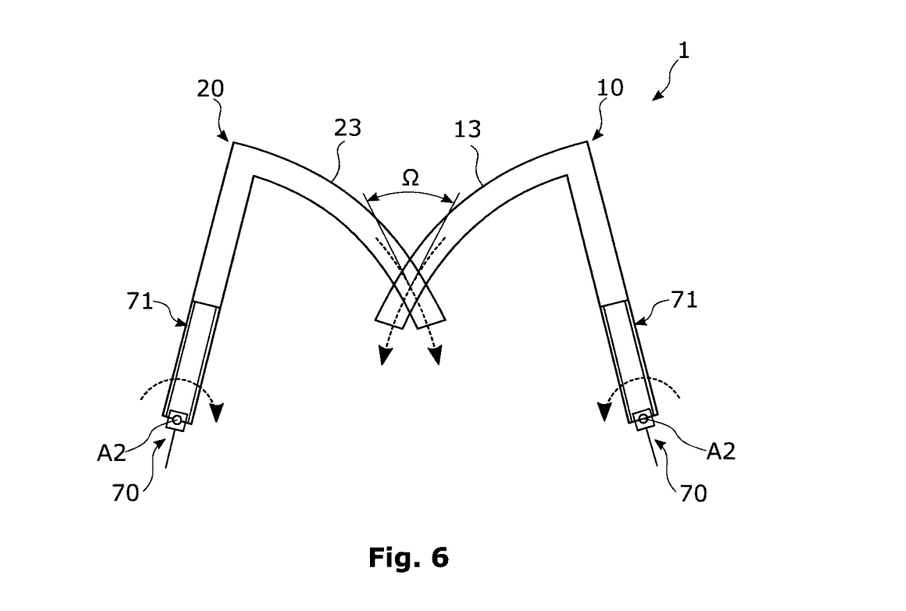
FIG. 6 shows a schematic view of a second movement of the spinal repositioning instrument.

Thus the instrument 1 can perform independently two different movements; the coupling bodies 10, 20 move in a plane common to both movements. FIGS. 5 and 6 show schematically the first and second movements respectively, wherein the instrument 1 is shown coupled to downtubes 71 and pedicle screws 70, in an arrangement suitable for minimally invasive surgery (described further below). The first movement (FIG. 5) is effectively a scissor-like pivoting about the crossing point A1 of the arc portions 13, 23. The crossing point A1 corresponds to a first axis. The second movement (FIG. 6) comprises a rotation of each coupling body 10, 20 about the centre A2 of its respective arc portion 13, 23. The centres A2 of the respective arc portions correspond to second axes.

In other words when only the second nut 6 is tightened, only the first movement is possible, wherein pivoting between the guides 30, 40 brings about a pivoting of the coupling bodies 10, 20 about the common rotation axis A1 of the pinion 50 which need not rotate.

In other words when the only the first nut 2 is tightened, only the second movement is possible; the movement of the first arc portion 13 along its guide 30 rotates the pinion 50 which in turn moves of the second arc portion 23 along its guide in the opposite direction of the first arc portion's movement but by the same amount. Because the relative angle between the guides is fixed, the angle $\Omega$ of the tangents of the arc portions 13, 23 where they run past each other is fixed. The second axes A2 are fixed relative to each other. Thus the movements of the coupling bodies 10, 20, even when seen relative to a stationary reference point (e.g. a surface on which the patient is lying) are reflectionally symmetric throughout the second movement. The second movement is configured to bring about reduction when the instrument 1 is coupled to two monoaxial pedicle screws 70 via optional downtubes 71, or to two locked polyaxial pedicle screws 70 via optional downtubes 71.

Referring again to FIG. 1, The instrument 1 may preferably be provided with a pushing/pulling means 60 to controllably effect the relative movement of the coupling bodies 10, 20 in the first and/or second movements. Such a pushing/pulling means 60 may comprise a threaded shaft (stud 60) which is inserted in stud nuts 62, 63 which are each pivotably fixed at the top of a respective column 14, 24 in a manner known in the art. Each pivot axis may be parallel to the first A1 and second A2 axes. The stud 61 comprises two threaded surfaces (the threads are not shown in the figures) on its outer periphery. One portion of the periphery is provided with a left-handed thread, while another portion is provided with a right-handed thread. Through-holes of each stud nut 62, 63 have corresponding threads. By rotating the stud 61 one way the stud nuts 62, 63 are pulled together. When turned the other way the stud nuts 62, 63 are pushed apart. The stud 61 is shown with a dashed line in FIG. 2 to improve clarity.

An example of an MIS (minimally invasive surgery) procedure in which the instrument 1 is used is described as follows with reference to FIG. 7, which schematically shows a dorsal view of two vertebral bodies 81, 82; adjacent and intermediate vertebral bodies are not shown. Four pedicle screws 70a-70d are fixed to the two vertebral bodies 81, 82, with a pedicle screw 70a-70d fixed to a pedicle of each vertebral body 81, 82. A downtube (not shown in FIG. 7) is attached to the tulip of each pedicle screw 70a-70d. A respective instrument 1a, 1b is coupled to the two downtubes 71 on each side of the spine, by coupling a first coupling body 10 to a first downtube 71's proximal end, and coupling the second coupling body 20 to a second downtube 71's proximal end. Therefore two instruments 1a, 1b are provided, with one for each side of the spine (left and right side in FIG. 7). Each instrument 1a, 1b is represented as a dashed-line rectangle in FIG. 7. The operation of each instrument 1a, 1b during repositioning is essentially identical, as explained in the following.

A distraction procedure corresponding to the first movement, and preferably performed before any reduction procedure, is described in the following. All four pedicle screws 70a-70d are unlocked, so that their tulips are free to pivot. The second nut 6 is fully tightened, and the first nut 2 is loosened on instruments 1a, 1b, so as to allow only the first movement.

Distraction is performed by rotating the coupling bodies 10, 20 so that their distal ends move apart, with rotation being about the first axis A1 (see FIG. 5). Controlled movements of the coupling bodies 10, 20 are performed by rotating the stud 61 in the direction that pulls the stud nuts 62, 63 together. Alternatively in a compression procedure the stud 61 is rotated in the opposite direction.

When the desired amount of distraction/compression has been achieved, the tulips on the pedicle screws 70a-70d are temporarily locked. The temporary locking and unlocking of the tulips may be performed by a suitably configured screwdriver (not shown) which is passed down the through-hole of each column 14, 24 and then though each downtube. The screwdriver head may be configured to securely hold a set screw and if necessary any coupling body serving as a rod substitute. The length of the screwdriver shank may be chosen so that it protrudes from the top of each column 14, 24 so as to allow rotation by hand via e.g. a handle. A screwdriver, set screw, and any rod substitute may be provided for each pedicle screw 70a-70d. Alternatively the instruments 1a, 1b may be used with downtubes and compatible pedicle screws that are configured to temporary lock the tulip even without a rod or set screw being inserted. A suitable arrangement is disclosed in WO2017194470 A1. The downtube components disclosed therein may be adapted in view of allowing operation when the instrument 1 is fixed to the downtube's proximal ends.

For both instruments 1a, 1b, the first nut 2 is fully tightened and the second nut 6 is loosened, to allow only the second movement. If a kyphosis reduction is required, the stud 61 is turned to bring the stud nuts 62, 63 together. Because the only motion that the instruments 1a, 1b allow is the second movement, each coupling body pivots about a respective second axis A2 (the second axes being parallel) which may preferably be at or near the tulip of the respective pedicle screw 70a-70d. The position of each second axis A2 may be selected by suitably sizing any of the instrument 1, downtube 71 and pedicle screw 70. While the second movement is performed, the distance between each ipsilateral pair of pedicle screws 70a, 70b; and 70c, 70d is maintained. In other words the distraction from the previous step is maintained.

With the sagittal curve of the spine repositioned, rods can now be fitted, the tulips locked, and the instruments 1a, 1b removed, but in order to maintain the new positions of the vertebral bodies 81, 82 even after removing the instruments 1a, 1b, the following steps may be performed.

Figure 7:
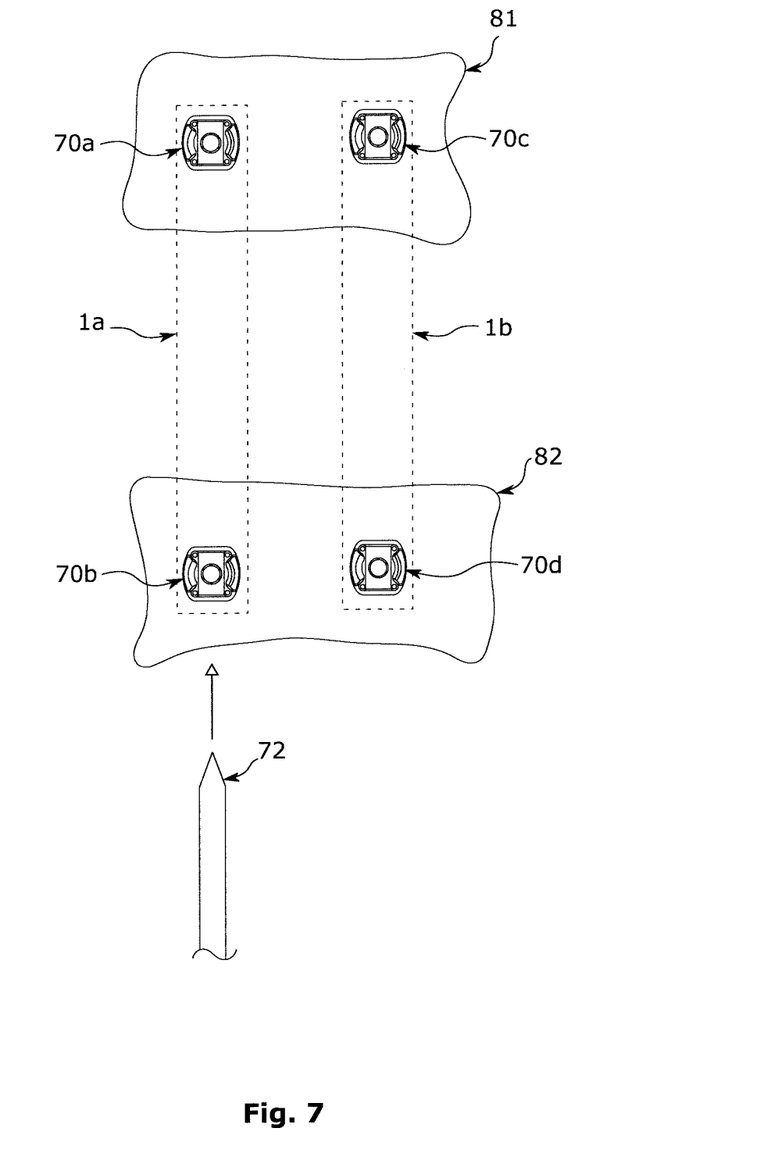
FIG. 7 shows a schematic view of two vertebral bodies on which a method according to an embodiment of the present disclosure is to be performed.

The tulips, which were all temporarily locked during the reduction, are unlocked for one side of the spine only (e.g. the left side in FIG. 7). The instruments 1a, 1b remain coupled to all tulips. The new position of the vertebral bodies 81, 82 is not lost because on the tulips-locked side of the spine (right side) two pedicle screws 70c, 70d are fixed from pivoting or displacing due to their respective locked tulips, while on the tulips-unlocked side of the spine (left side) two pedicle screws 70a, 70b are prevented from relatively displacing by the fixed spacing between their respective unlocked tulips. Since generally a plane may be defined (i.e. fixed in space) by an axis and a single point (which does not coincide with the axis), the vertebral bodies 81, 82 are fixed in respect of both displacement and rotation, in three dimensions, relative to each other.

With the tulips on the left side unlocked, any temporary set screw and rod substitute on that side can be removed with the instruments 1*a*, 1*b* still in place. A rod 72 is then inserted here and locked in place. The embodiment provides particular advantages here because with the left-side tulips unlocked, the insertion of the rod 72 (which does not have to be straight) is facilitated by the free polyaxiality. The relative orientations of the unlocked tulips may be adjusted through a further second movement of the instrument 1*a*/though freeing the second movement of the instrument 1*a*. A perpendicular adaptation between rod 72 and tulips is possible and allows a non-constrained fixation of the rod. With the pedicle screws 70*a*, 70*b* now locked by the rod 72 on the left side, their respective instrument 1*a* is removed.

The tulips for the remaining instrument 1*b* (right side in FIG. 7) are unlocked, with its instrument 1*b* still in place. The vertebral positions are once again maintained because the tulips are locked on the left side of the spine via the rod 72 (described above), and the distance between the right-side tulips, which are unlocked, is directly fixed by the remaining instrument 1*b*. With these tulips unlocked, the insertion of a second rod (not shown) is equally facilitated.

With the right-side tulips then locked, the remaining instrument 1*b* is now removed. The positions of the vertebral bodies 81, 82 are fixed purely by the locked pedicle screws 70*a*-70*d* and their rods.

The present embodiment has the following advantages.

The instrument 1 allows a large amount of reduction to be performed without an anterior-posterior shift of the vertebral bodies. This is because the rotation is symmetric. In other words the rotation closely matches a pivoting with the hinge being at the interposed damaged vertebral body. Shear forces on the vertebral bodies are reduced. The planning of the reduction step is less involved (e.g. with fewer iterations of taking x-rays between reductions).

Distraction (corresponding to the first movement) is performed without having to lock the tulips. Structural features to keep the coupling bodies both perpendicular to the coronal plane and parallel to each other are unnecessary.

Reduction can be performed with either monoaxial pedicle screws or locked polyaxial pedicle screws.

The instrument 1 is configured to block the first and second movements independently. The coupling bodies 10, 20 are restricted to move in only one plane. Therefore the first and second movements can be performed in isolation. Switching between the first and second movements requires merely tightening one nut and loosening another.

Many of the components are configured to guide both the first and second movements. For example the guides 30, 40 which slidingly receive the arc portions 13, 23 allow the second movement to be performed. Equally the pivoting between the guides 30, 40 allows the first movement to be performed. In other words the position at which the angle Ω between tangents of intersecting arcs is constant in the second movement serves also as the pivot for the first movement. As another example, the two movements use a common pushing/pulling means 60, so the construction is simplified compared to a reference example wherein each movement requires a respective mechanism with no commonality of parts and higher risk of jamming. The simplicity of the instrument's construction reduces the possibility of jamming.

The instrument 1 can be easily disassembled since there is one main screw that holds essentially all of the components together. Maintenance and sterilisation is facilitated.

Since the stud is provided with a left-handed thread and a right-handed thread, the weight distribution of the instrument 1 is balanced.

Any distraction or reduction performed by the instrument 1 can be removed by turning the stud in the opposite direction.

When the instrument 1 is used in pairs, with an instrument 1*a*, 1*b* provided on each side of the sagittal plane, rods can be inserted and the tulips locked without loss of the spinal reposition. So the transition between on the one hand spinal repositioning using the instruments 1*a*, 1*b*, and on the other hand the insertion of the rods, is facilitated. The instrument 1 allows the use of rods which are not straight.

In a comparative example, all pedicle tulips must remain locked to hold the position after the repositioning, and in some cases must always face each other so that only a straight rod (not a bent rod) can be used. Any downtube must be exactly parallel aligned so that the rod maintains its orientation in the locked screw. On the other hand some dorsal stabilization systems comprise polyaxial pedicle screws having tulips that can be temporarily locked via appropriate instruments, even without inserting a rod. When used with such a dorsal stabilization system, repositioning using the instruments 1 is facilitated.

The construction of the instrument 1 allows adaptation to both MIS and open surgery procedures.

The large range of kyphosis reduction allows the instrument 1 to be used for many diseases, including not just trauma but also degenerative diseases such as spondylolisthesis. The instrument 1 is easily adaptable to pedicle subtraction osteotomies (PSO).

Various modifications to the embodiment example are shown in the following examples.

The instrument 1 used in the above-described MIS procedure can be adapted for open surgery by mounting the coupling bodies 10, 20 of the instruments directly to the pedicle tulips rather than via the downtubes 71. The columns 14, 24 may be suitably adapted for receiving pedicle screw tulips and also the arc radius of the arc portions 13, 23 adjusted in view of the distance from the arc portions 13, 23 to the pedicle screw 70.

The rail 11, 21 is not limited to being provided with only one arc portion 13, 23. For example each rail may be provided with two concentric arc portions, each guided by a respective guide. In this way the instrument 1 is more robust and the first and second movements are less susceptible to deformation. The number of pinions may be adapted in view of the number of pairs of overlapping arc portions.

Disclosed is a repositioning instrument for spinal column surgery, in particular the minimally-invasive correction of spinal column fractures with the help of a dorsal stabilisation system comprising polyaxial screws and a temporary polyaxial clamping. The instrument has two coupling bodies for direct or indirect coupling to respective pedicle screws. The instrument can perform at least two kinematic movements: in the first the coupling bodies rotate about a common axis; in the second each coupling body rotates about a respective axis which is preferably at or near a vertebral body. These kinematic movements are independent so as to allow a separation of distraction and reduction.

The invention claimed is:

1. A spinal repositioning instrument comprising a first coupling body adapted for direct or indirect coupling to a pedicle screw, and a second coupling body adapted for direct or indirect coupling to another pedicle screw, wherein
   the spinal repositioning instrument is configured to perform a first movement for vertebral repositioning under which first movement the first and second coupling bodies are moved respectively for changing a distance between the pedicle screws when being coupled to the first and second coupling bodies and to perform a second movement for reduction independent from the first movement, under which second movement the coupling bodies are moved respectively for changing an angle between longitudinal axes of the pedicle screws when being coupled to the coupling bodies, a synchronizing mechanism or transmission is provided functionally linking the first and second coupling bodies with each other and being configured such that at least or exclusively the respective movements of the coupling bodies under the second movement are symmetrical to each other, and an adjustable linkage mechanism is provided connecting the two coupling bodies such that under the first movement the first and second coupling bodies perform a scissor-like pivoting about a first axis provided by the adjustable linkage mechanism in a first adjustment state of the adjustable linkage mechanism exclusively allowing a pivoting movement and under the second movement the first and second coupling bodies perform a rotation in opposite directions about respective second axes in a second adjustment state of the adjustable linkage mechanism allowing a translation movement of the first and second coupling bodies relative to each other wherein the respective second axes are relatively fixed to each other under the second movement.

2. The spinal repositioning instrument according to claim 1, wherein each coupling body comprises at least one column portion being adapted to get directly or indirectly coupled with a respective pedicle screw at its distal end portion and at least one arc portion having an arc center at the second axis of its respective coupling body and extending in a direction substantially perpendicular to the column portion, wherein the two arc portions are connected at the adjustable linkage mechanism.

3. The spinal repositioning instrument according to claim 2, wherein the adjustable linkage mechanism comprises a respective guide for slidingly guiding each arc portion to allow a relative movement of the arc portions along their longitudinal directions when the adjustable linkage mechanism is in the second adjustment state.

4. The spinal repositioning instrument according to claim 3, wherein the guides are pivotably connected, the pivot being at the first axis.

5. The spinal repositioning instrument according to claim 3, wherein under the second movement the synchronizing mechanism or transmission is configured to slide the two arc portions at the same rate under guidance from the adjustable linkage mechanism.

6. The spinal repositioning instrument according to claim 5, wherein the synchronizing mechanism or transmission comprises at least one pinion, wherein the two arc portions each comprise a rack surface, and the rack surfaces engage with the at least one pinion.

7. The spinal repositioning instrument according to claim 6, wherein the at least one pinion can spin about the first axis.

8. The spinal repositioning instrument according to claim 7, wherein the at least one pinion is accommodated in the guides.

9. The spinal repositioning instrument according to claim 6, wherein the at least one pinion is accommodated in the guides.

10. The spinal repositioning instrument according to claim 9 wherein an adjustment handle is provided which is functionally connected with the adjustable linkage mechanism to adjust the adjustable linkage mechanism selectively into the first or second adjustment state wherein in the first adjustment state the at least one pinion is locked to just allow the pivoting movement of the guides around the at least one pinion and in the second adjustment state the at least one pinion is released to allow the translation movement of the arc-like portions relative to each other along the rack surfaces with which the at least one pinion is engaged, respectively.

11. The spinal repositioning instrument according to claim 3, wherein under the second movement the synchronizing mechanism or transmission is configured to slide the two arc portions at the same rate under guidance from the adjustable linkage mechanism.

12. A spinal repositioning system, comprising at least two spinal repositioning instruments according to claim 1.

13. The spinal repositioning system according to claim 12, comprising at least four polyaxial pedicle screws.

14. The spinal repositioning system according to claim 13, wherein a respective polyaxial pedicle screw is directly or indirectly coupled to each coupling body, and the spinal repositioning system is configured to hold the relative position and orientation of two vertebral bodies even when two polyaxial pedicle screws that are directly or indirectly coupled to one of the instruments are unlocked.

15. A method of using the spinal repositioning system according to claim 12, comprising the steps of:
attaching two polyaxial pedicle screws to each one of two vertebral bodies;
coupling a first spinal repositioning instrument to the two polyaxial pedicle screws on one side of a spine;
coupling a second spinal repositioning instrument to the two pedicle screws on the other side of the spine; and
performing a reduction by moving the spinal repositioning instruments under their second movements with the four polyaxial pedicle screws locked.

16. The method according to claim 15, further comprising the steps of subsequently:
unlocking the polyaxial pedicle screws coupled to the first spinal repositioning instrument;
fixing the first movement of the first spinal repositioning instrument and allowing its second movement;
fixing the first and second movements of the second spinal repositioning instrument; and
inserting a rod into the tulips of the unlocked polyaxial pedicle screws.

17. A method of using the spinal repositioning instrument according to claim 1, comprising the steps of:
attaching two pedicle screws to two vertebral bodies, with one pedicle screw for each vertebral body;
coupling each coupling body to a pedicle screw via a respective downtube; and
performing a reduction by moving the spinal repositioning instrument under the second movement.

18. The spinal repositioning instrument according to claim 1, wherein the synchronizing mechanism or transmission is a pinion-tooth rack-transmission.

* * * * *